US012729188B2

(12) United States Patent
Bonrath et al.

(10) Patent No.: US 12,729,188 B2
(45) **Date of Patent: *Sep. 8, 2026**

(54) RING CLOSURE OF BENZOQUINONES CONTAINING AN UNSATURATED SIDE CHAIN USING A BASIC CATALYST

(71) Applicant: DSM IP Assets B.V., Heerlen (NL)

(72) Inventors: Werner Bonrath, Kaiseraugst (CH); Rolf Kuenzi, Kaiseraugst (CH); Meltem Tirpanci, Kaiseraugst (CH); Thomas Netscher, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 379 days.

This patent is subject to a terminal disclaimer.

(21) Appl. No.: 18/557,241

(22) PCT Filed: Apr. 26, 2022

(86) PCT No.: PCT/EP2022/061095

§ 371 (c)(1),
(2) Date: Oct. 25, 2023

(87) PCT Pub. No.: WO2022/229215

PCT Pub. Date: Nov. 3, 2022

(65) Prior Publication Data

US 2024/0217941 A1 Jul. 4, 2024

(30) Foreign Application Priority Data

Apr. 28, 2021 (EP) .................................... 21170913

(51) Int. Cl.
*C07D 311/72* (2006.01)
*C07D 311/92* (2006.01)

(52) U.S. Cl.
CPC .......... *C07D 311/72* (2013.01); *C07D 311/92* (2013.01)

(58) Field of Classification Search
CPC ............................ C07D 311/72; C07D 311/92
See application file for complete search history.

(56) References Cited

U.S. PATENT DOCUMENTS 3,064,012 A 11/1962 Karl et al.
3,154,565 A 10/1964 Linn et al.
(Continued)

FOREIGN PATENT DOCUMENTS

GB 870638 A 6/1961
GB 877960 A 9/1961
(Continued)

OTHER PUBLICATIONS

Venkateswarlu et al.; Three New Heptaprenylhydroquinone Derivatives From the Sponge Ircinia Fasciculata; J. Nat. Prod., 57, 1994, 1286-1289.*

(Continued)

*Primary Examiner* — Sarah Pihonak
*Assistant Examiner* — Jackson J Hernandez
(74) *Attorney, Agent, or Firm* — NIXON & VANDERHYE P.C.

(57) ABSTRACT

The present invention relates to the formation of compound of the formula (I) by a ring closure reaction of the compound of the formula (II) in the presence of a catalytic amounts of a base. It has been found that this reaction is very efficient and offers for example an efficient pathway for the synthesis of 3,4-dehydro-α-tocotrienol respectively α-tocotrienol and α-tocopherol.

(Continued)

(I)

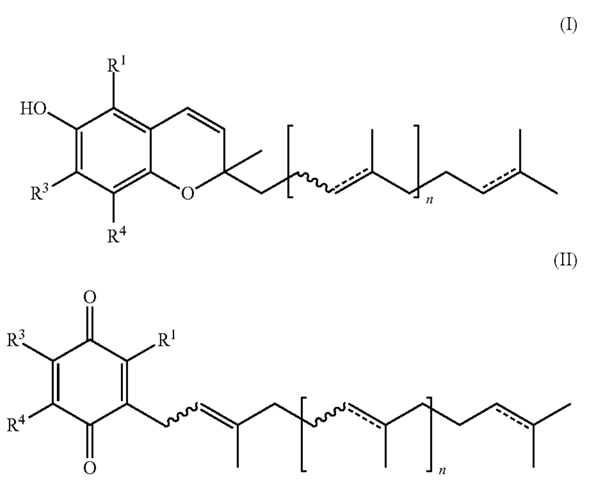

(II)

13 Claims, 1 Drawing Sheet

(56) References Cited

U.S. PATENT DOCUMENTS

| | | | |
|---|---|---|---|
| 2005/0038269 | A1* | 2/2005 | Giraudi et al. |
| 2005/0171362 | A1* | 8/2005 | Bonrath et al. |
| 2005/0277777 | A1* | 12/2005 | Bonrath et al. |

FOREIGN PATENT DOCUMENTS

| | | | |
|---|---|---|---|
| GB | 947643 | A | 1/1964 |
| JP | S52111576 | A | 9/1977 |
| JP | H05156247 | A | 6/1993 |
| WO | 2005054223 | A2 | 6/2005 |

OTHER PUBLICATIONS

Chan et al.; Bio-inspired dimerisation of prenylated quinones directed towards the synthesis of the meroterpenoid natural products, the scabellones; Tetrahedron Letters, 56, 2015, 1486-1488.*

Odinokov et al.; Chemistry of Natural Compounds, Bioorganic, and Biomolecular Chemistry; Izvestiya Akademii Nauk. Seriya Khimicheskaya, 3, 2002, 489-492.*

Dotz et al, "Carbonyl(carben)-Komplex-induzierte Synthese von Vitaminen der Kl-und K 2-R e i he Carbonyl Carbene Complex Induced Synthesis of Vitamins of the K, and K, Series", Retrieved from the Internet: URL:https://chemistry-europe.onlinelibrary .wiley. com/doi/10.1002/cber.19821150404, Jan. 1, 1982, pp. 1278-1285, Chem. Ber.

Evans et al, "Coenzyme Q. XXXVII. Cyclization of coenzyme Q to the corresponding chromenols with sodium hydride", Retrieved from the Internet: URL:https://pubs.acs.org/doi/pdf/10.1021/ja00885a034, Jan. 1, 1963, pp. 239-240, J. Am. Chem. Soc.

Evans et al., pKa's Table, Chem 206, 5 pages.

Gille Lars et al:, "Ubichromanol: A prodrug to support mitochondrial ubiquinone functions?", Biofactors, Oxford University Press, Oxford, Jan. 1, 2008, pp. 83-90, vol. 32, No. 1-4.

Kenji Terashima et al, "Powerful antioxidative agents based on garcinoic acid from Garcinia kola", Bioorganic & Medicinal Chemistry, Elsevier, May 1, 2002, pp. 1619-1625, vol. 10, No. 5.

Lien et al, "Original Contribution Quantitative Structure-Activity Relationship Analysis of Phenolic Antioxidants", Retrieved from the Internet: URL:https://www.sciencedirect.com/science/article/pii/S0891584998001907?via%3Dihub, Jan. 1, 1999, pp. 285-294, ELSEVIER.

Links et al, "The conversion of ubiquinone to ubichromenol", Biochimica et Biophysica Acta, Elsevier, Jan. 1, 1960, pp. 193-194, vol. 38.

Pearce et al, "Inhibitors of Cholesterol Biosynthesis. 2. Hy}ocholesterolemic and Antioxidant Activities of Benzopyran and Tetrahydronaphthalene Analogues of the Tocotrienols.Opyran and Tetrahydronaphthalene", Journal of Medicinal Chemistry, Feb. 18, 1994, pp. 526-541, vol. 37, No. 4, American Chemical Society.

Schudel et al., Helvetica Chimica Acta, vol. XLVI, Fasciculus vii (1963)—No. 281., pp. 2517-2526.

International Search Report for PCT/EP2022/061095 mailed Sep. 12, 2022, 8 pages.

Written Opinion of the ISA for PCT/EP2022/061095 mailed Sep. 12, 2022, 9 pages.

Kelly, Craig A. et al., "Estimates of hydride ion stability in condensed systems: energy of formation and solvation in aqueous and polar-organic solvents", Phys. Chem. Chem. Phys., 2001, 3, 2086-2090.

Notice of First Examination Action, CN Application No. 202280030782.6, Sep. 29, 2025.

* cited by examiner

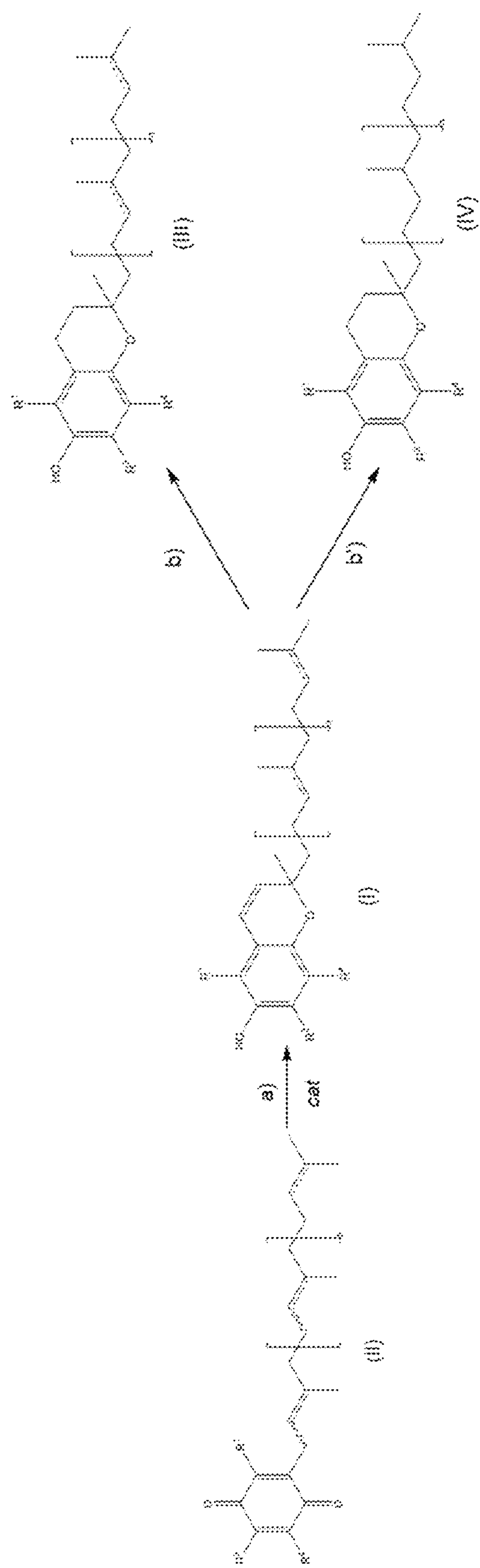
(III)
(IV)
b)
b')
(I)
a)
cat
(II)

RING CLOSURE OF BENZOQUINONES CONTAINING AN UNSATURATED SIDE CHAIN USING A BASIC CATALYST

CROSS-REFERENCE TO RELATED APPLICATIONS

This application is the U.S. national phase of International Application No. PCT/EP2022/061095 filed Apr. 26, 2022 which designated the U.S. and claims priority to EP 21170913.4 filed Apr. 28, 2021, the entire contents of each of which are hereby incorporated by reference.

TECHNICAL FIELD

The present invention relates to the field of the synthesis of chromanes and chromenes, particularly, of 3,4-dehydrotocopherols, 3,4-dehydrotocotrienols, tocopherols and tocotrienols.

BACKGROUND OF THE INVENTION

An important class of chromane compounds are vitamin E and its esters. A synthetic pathway for chromanes is via their corresponding chromenes.

There exist different routes for the formation of chromenes.

Schudel, Mayer, Isler, *Helv. Chim. Acta* 46, 2517-2526 (1963) discloses the formation of 3,4-dehydro tocotrienols by a ring closure reaction of geranylgeranyl trimethyl benzoquinone in the formation of chromenes by ring closure in pyridine as reaction medium, i.e. pyridine is present in large amounts (corresponding to a huge excess relative to the amount of the benzoquinone). As pyridine is a compound, cancerogenic to animals and highly inflammable compound, its use is very unfavourable, particularly in high amounts. Furthermore, the reaction mixture obtained is a complex mixture and the isolation of the desired product requires a complex derivatisation procedure forming the dehydrotocotrienol-p-phenylazobenzoate for separation and purification by crystallisation. For this procedure the very expensive and highly toxic chemical 4-(phenylazo)benzoyl chloride is used and, therefore, this process is overall very disadvantageous.

Also Dötz K. H. et al., *Chem. Ber.* 115, 1278-1285 (1982) and Terashima K. et al, *Bioorganic & Medicinal Chemistry* 10, 1619-1625 (2002) disclose a cyclisation reaction by refluxing a respective benzoquinone in a huge molar excess of pyridine.

WO 2015/028643 A1 discloses the formation of chromenes by Au(I) or Ag(I) catalysed intramolecular hydroarylation of chiral aryl alkynes. Gold and silver catalyst are very expensive.

SUMMARY OF THE INVENTION

Therefore, the problem to be solved by the present invention is to offer a process to provide chromenes and chromanes in a manner which avoids the use of high amounts of pyridine or bases in general.

This problem has been solved by the process according to claim 1. It has been particularly found that bases can be used in catalytical amounts for the ring closure reaction of benzoquinones of the formula (II) to yield the chromenes of the formula (I). It has been particularly found that catalyst which are strongly basic are particularly suitable as catalytic bases for said ring closure reaction. It has been found that the compound of the formula (I) can be obtained in very high conversions and yields.

This process offers a very favourable synthetic pathways to chromanes of the formula (III) or (IV) according to the claim 8 or 9.

Further aspects of the invention are subject of further independent claims. Particularly preferred embodiments are subject of dependent claims.

BRIEF DESCRIPTION OF THE DRAWING

FIG. 1 shows a ring closing step a) of the compound of the formula (II) in the presence of a basic catalyst ("cat") to yield the compound of the formula (I), and alternatively hydrogenation steps b) and b') to yield the a partially hydrolysed compound of formula (III) and a completely hydrolysed compound of formula (IV), respectively.

DETAILED DESCRIPTION OF THE INVENTION

In a first aspect, the present invention relates to a process of manufacturing the compound of the formula (I)

(I)

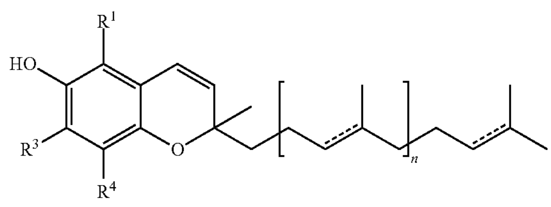

comprising a ring closing step of the compound of the formula (11)

(II)

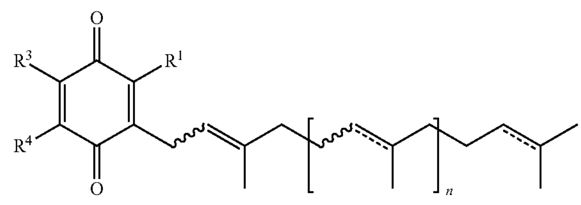

in the presence of a basic catalyst to yield the compound of the formula (I), wherein n=0 or 1 or 2 or 3 or 4 or 5 or 6 or 7 or 8 or 9 or 10 or 11 or 12;

$R^1$ represents hydrogen or a methyl group;

$R^3$ and $R^4$ either represent independently from each other hydrogen or methyl group or methoxy group or represent together a —CH—CH—CH— and form an aromatic group;

any bond having dotted line (------) represents independently from each other either a carbon-carbon single bond or a carbon-carbon double bond; and any wavy line represents independently from each other a carbon-carbon bond and which when linked to the carbon-carbon double bond is either in the Z- or in the E-configuration;

characterized in that the molar ratio of the basic catalyst to the compound of the formula (I) is 1:1'000 to 1:5, particularly 1:100 to 1:10.

For sake of clarity, some terms used in the present document are defined as follows:

In the present document, a "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example $-CH(CH_3)-CH_2-CH_3$ is considered as a $C_4$-alkyl group.

In case identical labels for symbols or groups are present in several formulae, in the present document, the definition of said group or symbol made in the context of one specific formula applies also to other formulae which comprises the same said label.

The term "independently from each other" in this document means, in the context of substituents, moieties, or groups, that identically designated substituents, moieties, or groups can occur simultaneously with a different meaning in the same molecule.

In the present document, any dotted line in formulae represents the bond by which a substituent is bound to the rest of a molecule.

In the present document any bond having dotted line (------) in a chemical formula represents independently from each other either a carbon-carbon single bond or a carbon-carbon double bond.

Any wavy line in any formula of this document represents a carbon-carbon bond and which when linked to the carbon-carbon double bond is either in the Z or in the E-configuration. It is preferred in all molecules that the carbon-carbon double bond is in the E-configuration.

The "$pK_a$" is commonly known as negative decadic logarithm of the acid dissociation constant ($pK_a=-\log_{10} K_a$). When the organic acid has several protons the $pK_a$ as used in this document relates to the dissociation constant of the last proton. For example, for a base having two basic sites the "pka" relates to $pK_{a2}$. The $pK_a$ are measured at standard temperature and pressure.

Compound of the Formula (II)

The compounds of the formula (II) are substances as well as their synthesis is known to the person skilled in the art.

(II)

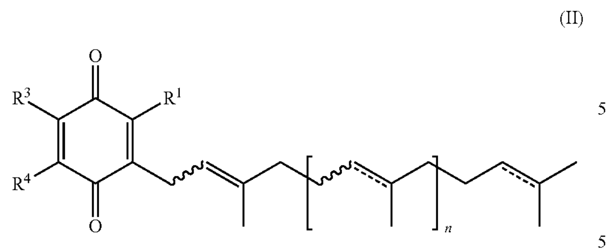

In one preferred embodiment, the substituent $R^3$ and $R^4$ represent methoxy groups. In this embodiment any bond having dotted line (------) represents preferably a carbon-carbon double bond, which is preferably in the E-configuration.

Ubiquinones are important representatives of this embodiment. The ubiquinones are denoted according to the number of isoprenoid groups in the side chain as ubiquinone-2 (n=0), ubiquinone-3 (n=1), ubiquinone-4 (n=2), ubiquinone-5 (n=3), ubiquinone-6 (n=4, ubiquinone-7 (n=5), ubiquinone-8 (n=6), ubiquinone-9 (n=7) and ubiquinone-10 (n=8). The ubiquinones are also known under the old term coenzyme Q. Ubiquinone-10 (n=8) (=coenzyme Q10) is a particular preferred species of this embodiment.

In another preferred embodiment, the substituents $R^3$ and $R^4$ represent either H or methyl groups. It is preferred that $R^3=R^4=CH_3$ It is particularly preferred that $R^1=R^3=R^4=CH_3$.

It is preferred that n=2. It is further preferred that all bonds having dotted line (------) in formula (II) are carbon-carbon double bonds, and preferably all in the E-configuration.

It is preferred in this embodiment that the compound of the formula (II) is the compound of the formula (II-BB)

(II-BB)

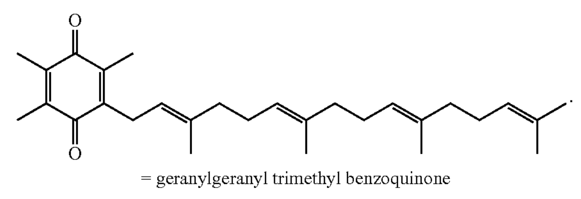

= geranylgeranyl trimethyl benzoquinone

In another preferred embodiment, the substituent $R^3$ and $R^4$ represent together a $-CH-CH-CH-$ and form an aromatic group. The compounds of this embodiment are represented by

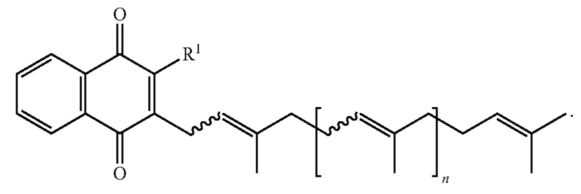

In this embodiment, $R^1$ represents preferably a methyl group.

Vitamin K1 (phylloquinone) is one example of this embodiment.

Menaquinones (MK), also known as vitamin K2, are further important representatives of this embodiment.

Any bond having dotted line (------) represents preferably a carbon-carbon double bond, which is preferably in the E-configuration The menaquinones are denoted according to the number of isoprenoid groups in the side chain as MK-2 (n=0), MK-3 (n=1), MK-4 (n=2), MK-5 (n=3), MK-6 (n=4), MK-7 (n=5), MK-8 (n=6), MK-9 (n=7), MK-10 (n=8), MK-11 (n=9), MK-12 (n=10) and MK-13 (n=11).

MK-4 (n=2) is a particular preferred species of this embodiment.

In case that any of the bond having dotted line (------) represents a carbon-carbon double bond, the formation of secondary ring formation (via existing carbon-carbon double bonds) by the existing a risk of would be expected by the person skilled in the art. As this has not been observed, it is particularly preferred that at least one of the bonds having dotted lines represents a carbon-carbon double bond. Therefore, this process particularly leads to α-tocotrienol, which has three double bonds in the side chain. αTocotrienol is an important compound in natural vitamin E.

Basic Catalyst

The process comprises a ring closing step of the compound of the formula (II) in the presence of a basic catalyst ("cat") to yield the compound of the formula (I) as depicted as step a) in the reaction scheme of FIG. 1.

The basic catalyst is preferably a hydroxide or a carbonate, preferably a hydroxide, of an alkali metal or an earth alkali metal, particularly an alkali metal hydroxide.

Furthermore preferred is that the basic catalyst is an organic amine, particularly an organic tertiary amine.

The basic catalyst is a base. Not all bases work equally well for the present invention. It is preferred that the basic catalyst is not pyridine. It has been shown that the conjugated acids of said basic catalysts having a $pK_a$ of between 8.6 and 15.7, particularly of between 9 and 15.7, measured in water, are particularly suitable. This means that the basic catalyst has preferably a $pK_b$ of between 5.4 and 0, particularly of between 5 and 0.

A few examples of $pk_a$ of the corresponding acids for:

| Base | pka[1] |
|---|---|
| 1,5-diazabicyclo[4.3.0]non-5-ene (=DBN) | 13.42[3] |
| 1,8-diazabicyclo[5.4.0]undec-7-ene (=DBU) | 12[2], 13.28[3] |
| 1-azabicyclo[2.2.2]octane (=quinuclidine) | 11[2], 10.95[3] |
| 4-(dimethylamino)pyridine (=DMAP) | 9.2[2], 9.7[3] |
| sparteine | 9.45[2] |
| 1,4-diazabicyclo[2.2.2]octane (=DABCO) | 8.8[2], 8.82[3] |
| NaOH | 15.7[2] |
| $Na_2CO_3$ | 10.4[3] |
| morpholine[4] | 8.36[2], 8.49[3] |
| triethanolamine[4] | 7.76[3] |
| pyridine[4] | 5.23[2], 5.23[3] |

[1]pka of the corresponding conjugated acid

[2]H. Ripin; D. A. Evans (2002). "$pK_a$'s of Nitrogen Acids" organicchemistrydata.org/hansreich/resources/pka/pka_data/evans_pKa_table.pdf

[3]www.aatbio.com/data-sets/pka-and-pkb-reference-table

[4]basic catalysts which are less preferred ($pk_a$ < 8.6)

In one embodiment the basic catalyst is an organic amine, particularly selected from the group consisting of 4-dimethylaminopyridine (=DMAP), 1,8-diazabicyclo[5.4.0]undec-7-ene (=DBU), 1,5-diazabicyclo[4.3.0]non-5-ene (=DBN), 1,4-diazabicyclo[2.2.2]octane (=DABCO), 1-azabicyclo[2.2.2]octane (=quinuclidine) and sparteine, preferably from the group consisting of 4-dimethylaminopyridine (=DMAP), 1,8-diazabicyclo[5.4.0]undec-7-ene (=DBU) and 1-azabicyclo[2.2.2]-octane (=quinuclidine).

In another embodiment the basic catalyst is preferably a hydroxide or a carbonate, preferably a hydroxide, of an alkali metal or an earth alkali metal, particularly an alkali metal hydroxide. In this embodiment, most preferably, the basic catalyst is NaOH or KOH.

The base is particularly not a hydride, such as sodium hydride, as hydrides form molecular hydrogens when contacted with the compounds of the formula (II). The formation of hydrogen leads to significant safety risks in the ring closing step and generally in processing.

When the base is used as solid, it is preferred that a phase transfer agent is used, particularly a quaternary ammonium salt, particularly of the formula $[NR_4]X$ wherein R is a $C_{2-18}$-alkyl group, particularly a $C_{3-8}$-alkyl group, and X is a halide. Preferably, the phase transfer agent is a tetrabutyl ammonium halide, particularly tetrabutyl ammonium bromide. Said phase transfer agent is preferably used in amounts of 0.1 to 10 mol %, particularly of 0.5 to 2 mol %, relative to the compound of formula (II).

In the case where the basic catalyst is an alkali metal hydroxide, in another embodiment, water can be present.

It is preferred that the ring closing step is performed in a hydrocarbon solvent, particularly in toluene.

In case a hydrocarbon solvent is used, the solvent is preferably used in such an amount that the solution with the compound of the formula (II) is between 0.05 and 5 molar, more preferred between 0.1 and 1 molar, in respect to the compound of the formula (II).

In case of water being present, it is preferred that the ring closure reaction is performed in a two-phase system, i.e. water phase and organic phase, particularly with a water and organic solvent phase It is important to stress that the basic substance is present in catalytical amounts, i.e. the basic catalyst is not present in stoichiometric amounts relative to the compound of the formula (II), but in significantly lower amounts, i.e. the molar ratio of the basic catalyst to the compound of the formula (I) is 1:1'000 to 1:5, particularly 1:100 to 1:10.

The ring closing step is typically performed under stirring preferably at a temperature of between 40 and 200° C., preferably between 90 and 150° C., more preferably at the reflux temperature of the organic solvent when an organic solvent is used, and/or at a pressure of between 1 bara and 10 bara. It is further preferred that this reaction is performed under inert atmosphere, preferably under nitrogen.

It has been shown that said process smoothly yields the compound of the formula (I).

(I)

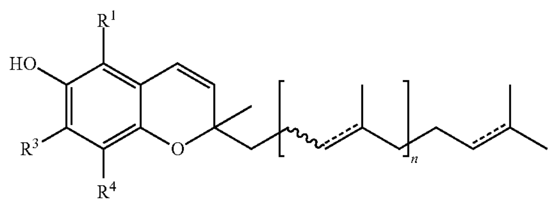

Particularly, said process allows the isolation of the desired compound of the formula (I) in a simple way, i.e. without the need of any complex derivatization followed by purification by crystallization and chemically transforming of the derivate finally to the desired compound as it is the case in the process as disclosed by Schudel, Mayer, Isler, Helv. Chim. Acta 46, 2517-2526 (1963).

Particularly preferred embodiments of the compound of the formula (I) are the compounds of the formula (I-A), (I-B) and (I-C), preferably the compound of the formula (I-AA), (I-BB), (I-CC1) and (1-CC2):

(I-A)

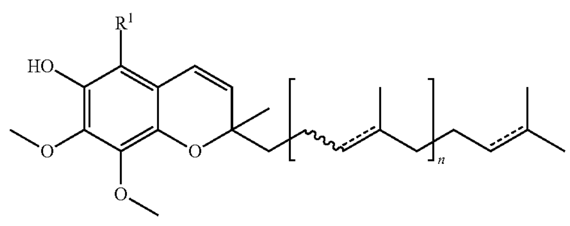

n = 0-9, particularly n = 8

-continued (I-AA)

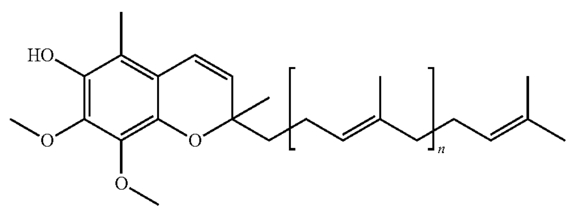

n = 0-9, particularly n = 8

(I-B)

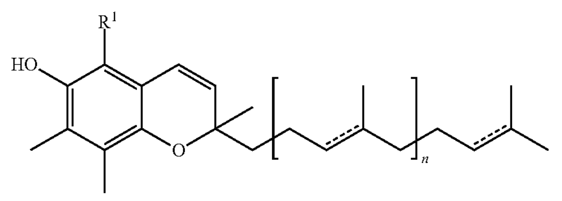

n = 0-9, particularly n = 2

(I-BB)

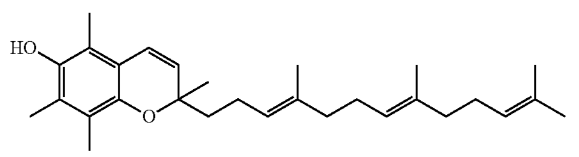

(I-C)

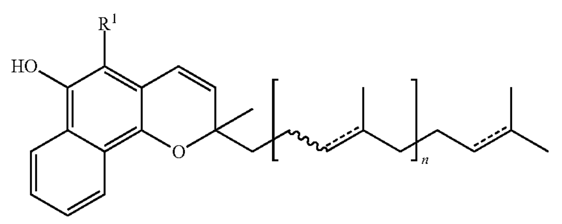

n = 0-12

(I-CC1)

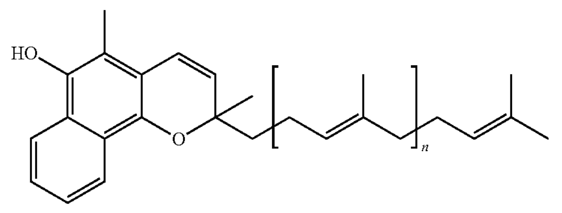

n = 0-12, particularly n = 2

(I-CC2)

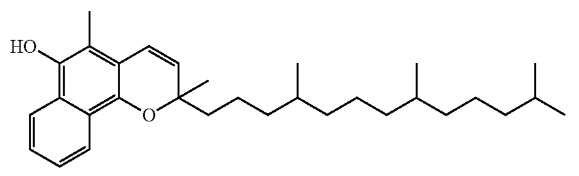

Very preferred compounds are the compounds of formula (I-As)

(I-As)

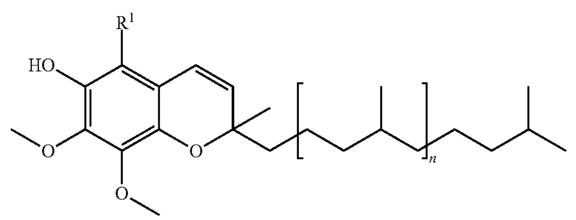

n = 3-9, particularly n = 8

Very preferred compounds are the compounds of formula (I-Cis)

(I-Cis)

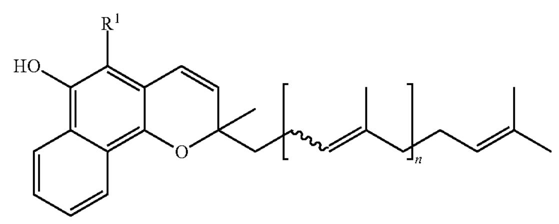

n = 1-12, particularly n = 2-5.

The compound of the formula (I) obtained as shown above can be hydrogenated by means of a hydrogenation agent.

In one embodiment, in this hydrogenation only the carbon-carbon double bond in the ring is hydrogenated whereas the olefinic carbon-carbon double bonds are not hydrogenated ("partial hydrogenation"), so that the hydrogenation leads to the compound of the formula (III) as depicted as step b) in the reaction scheme of FIG. 1.

(III)

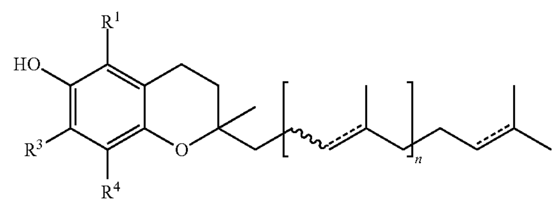

Particularly preferred embodiments of the compound of the formula (III) are the compounds of the formula (III-A), (III-B) and (III-C), preferably the compound of the formula (III-AA), (III-BB), (III-CC1) and (III-CC2):

(III-A)

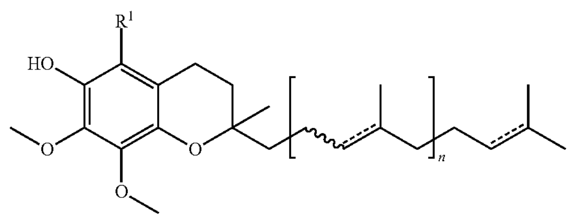

n = 0-9, particularly n = 8

(III-AA)

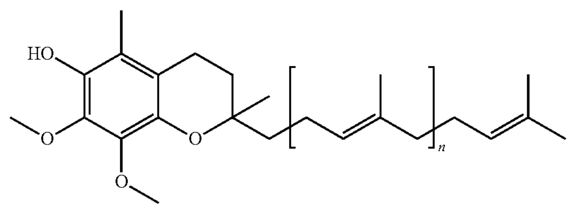

n = 0-9, particularly n = 8

(III-B)

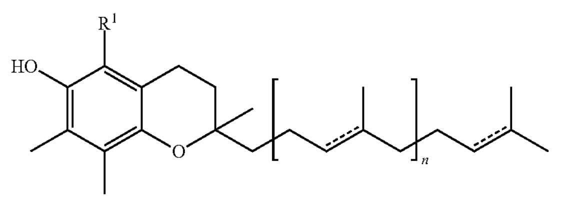

n = 0-9, particularly n = 2

(III-BB)

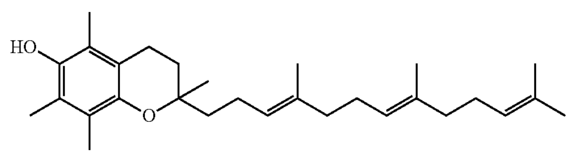

(III-C)

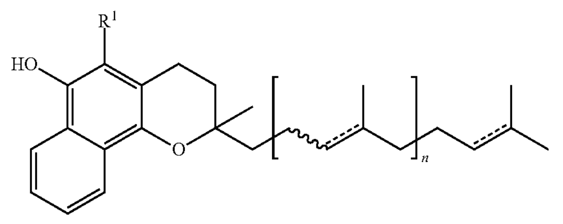

n = 0-12

(III-CC1)

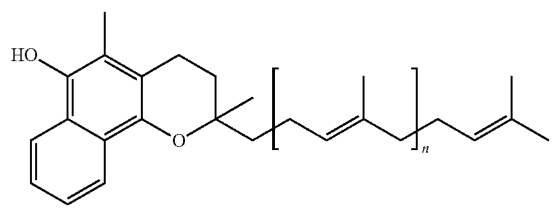

n = 0-12, particularly n = 2

-continued (III-CC2)

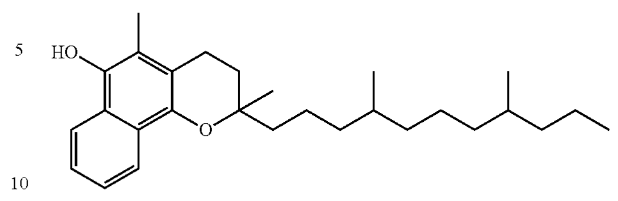

Very preferred compounds are the compounds of formula (III-Cis)

(III-Cis)

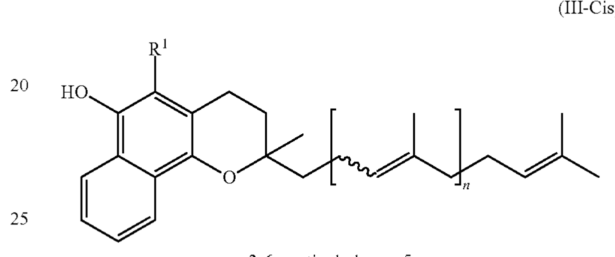

n = 3-6, particularly n = 5.

In another embodiment, in this hydrogenation all olefinic carbon-carbon double bonds are hydrogenated ("complete hydrogenation") so that the hydrogenation leads to the compound of the formula (IV) as depicted as step b') in the reaction scheme of FIG. 1.

(IV)

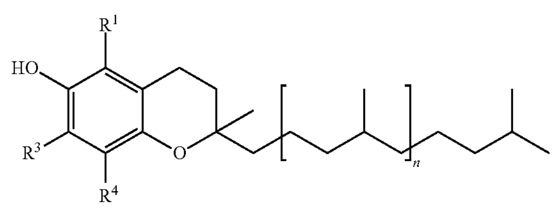

Particularly preferred embodiments of the compound of the formula (IV) are the compounds of the formula (IV-A), (IV-B) and (IV-C), preferably the compound of the formula (IV-A), (IV-BB) and (IV-CC):

(IV-A)

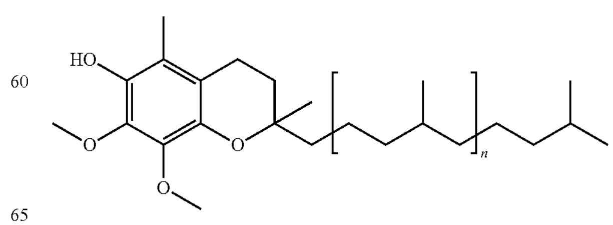

n = 0-9, particularly n = 8

-continued (IV-B)

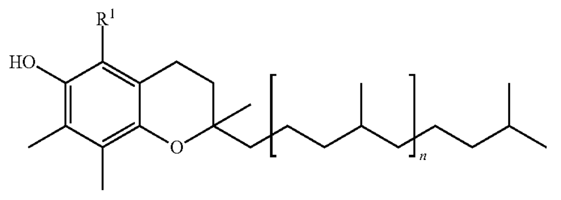

n = 0-9, particularly n = 2

(IV-BB)

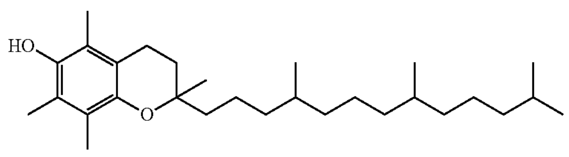

(IV-C)

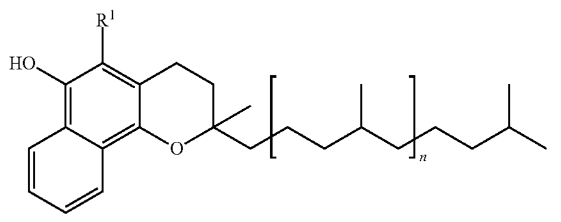

n = 0-12

(IV-CC)

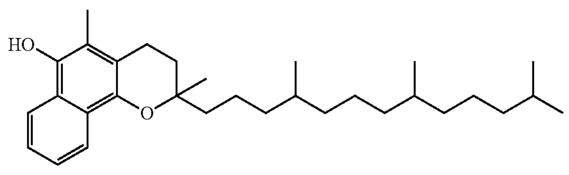

Very preferred compounds are the compounds of formula (IV-Cs)

(IV-Cs)

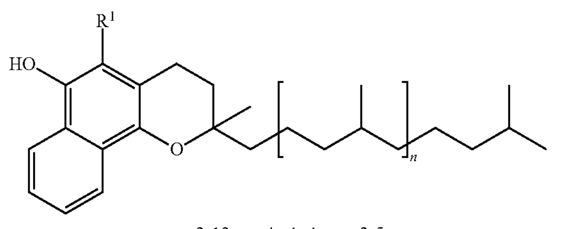

n = 3-12, particularly n = 3-5.

Hence, in a further aspect, the present invention also relates to a process of manufacturing a compound of the formula (III)

(III)

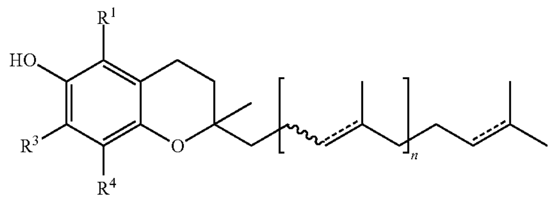

comprising the steps a) manufacturing the compound of the formula (I) by a process as discussed above in great detail;

(I)

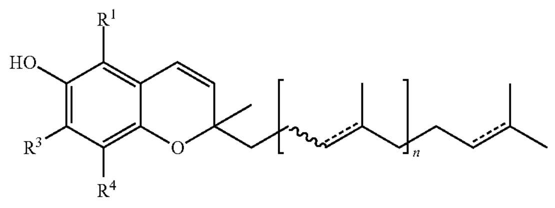

wherein any bond having dotted line (------) re resents independently from each other either a carbon-carbon single bond or a carbon-carbon double bond; and any wavy line represents independently from each other a carbon-carbon bond and which when linked to the carbon-carbon double bond is either in the Z- or in the E-configuration;

b) partially hydrogenating the compound of the formula (I) by means of a hydrogenating agent suitable for partial hydrogenation to yield the compound of the formula (III).

The hydrogenating agent used in step b) is a hydrogenating agent which only hydrogenates the carbon-carbon double bond of the ring in formula (I). Particularly suitable as hydrogenating agent is sodium/ethanol such as described by Schudel, Mayer, Isler, Helv. Chim. Acta 46, 2517-2526 (1963), particularly in the last paragraph on page 2524.

Hence, in a further aspect, the present invention also relates to a process of manufacturing a compound of the formula (IV)

(IV)

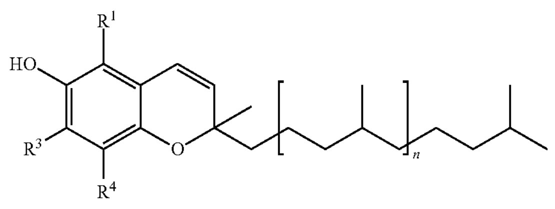

comprising the steps a) manufacturing the compound of the formula (I) by a process as discussed above in great detail (I)

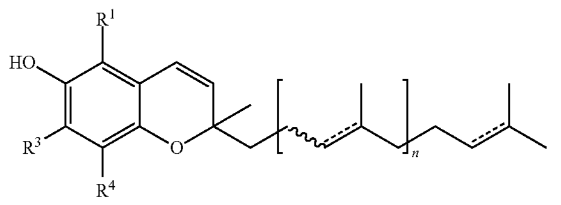

wherein any bond having dotted line (------) represents independently from each other either a carbon-carbon single bond or a carbon-carbon double bond; and any wavy line represents independently from each other a carbon-carbon bond and which when linked to the carbon-carbon double bond is either in the Z- or in the E-configuration;

b') hydrogenating the compound of the formula (I) by means of a hydrogenating agent to yield the compound of the formula (IV).

The hydrogenating agent used in step b') is a hydrogenating agent which hydrogenates all olefinic carbon-carbon double bond of the ring in formula (I). Particularly suitable as hydrogenating agent is hydrogen in the presence of a transition metal from the groups 7, 8, 9 or 10, particularly selected form the group consisting of Pd, Pt, Rh, Ru, Mn, Fe, Co, and Ni, more preferably Pd.

The heterogenous transition metal catalyst is preferably a heterogenous supported transition metal catalyst.

In this embodiment, the transition metal is supported on a carrier, i.e. palladium is attached to/or deposited on a carrier. The carrier is a solid material.

Preferably said carrier is carbon or an inorganic carrier. Preferred inorganic carriers are oxides or carbonates. Preferred oxides are oxides of Si, Al, Ce, Ti or Zr, particularly of Al or Si. Particularly preferred are silicon dioxide, alumina and titanium dioxide and ceria.

In case the support is Ce, the preferred oxide is $CeO_2$. Preferably, the oxide of Al is $Al_2O_3$ and AIO(OH). Particularly preferred is $Al_2O_3$.

It is preferred to perform the hydrogenation under pressure, particularly under a hydrogen pressure of 2 to 20 bar. It is further preferred to perform the hydrogenation at a temperature between 0° C. and 100° C.

The composition comprising the compound of the formula (II) and the basic catalyst itself is also an object of the present invention.

Hence, in a further aspect, the invention relates to a composition comprising i) a compound of the formula (II)

(II)

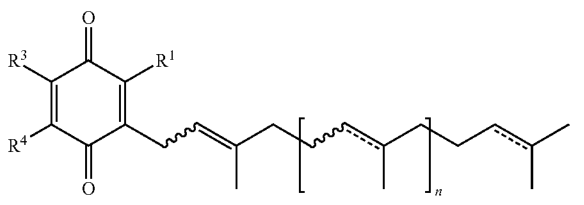

wherein n=0 or 1 or 2 or 3 or 4 or 5 or 6 or 7 or 8 or 9 or 10 or 11 or 12;

$R^1$ represents hydrogen or a methyl group;

$R^3$ and $R^4$ either represent independently from each other hydrogen or methyl group or methoxy group or represent together a —CH—CH—CH— and form an aromatic group;

any bond having dotted line (------) represents independently from each other either a carbon-carbon single bond or a carbon-carbon double bond; and any wavy line represents independently from each other a carbon-carbon bond and which when linked to the carbon-carbon double bond is either in the Z- or in the E-configuration; and ii) a basic catalyst;

characterized in that the molar ratio of the basic catalyst to the compound of the formula (I) is 1:1'000 to 1:5, particularly 1:100 to 1:10.

The compound of the formula (II) and the basic catalyst as well their preferred embodiments have been already discussed above in great detail for the process.

Within this invention, it has been found that a catalytical amount of base can be used for an efficient ring closure in the above ring closure step.

Hence, in a further aspect, the invention relates to a catalytical use of base for the ring closure reaction of the compound of the formula (II) to yield the compound of the formula (I)

(II)

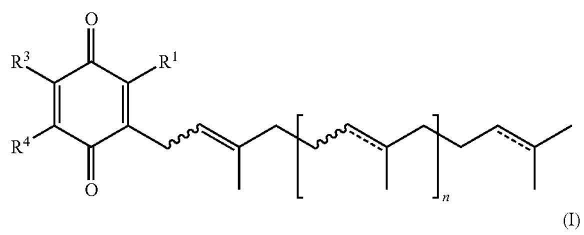

(I)

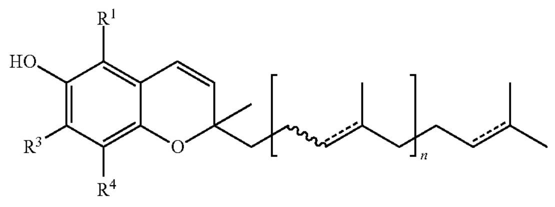

wherein n=0 or 1 or 2 or 3 or 4 or 5 or 6 or 7 or 8 or 9 or 10 or 11 or 12;

$R^1$ represents hydrogen or a methyl group;

$R^3$ and $R^4$ either represent independently from each other hydrogen or methyl group or methoxy group or represent together a —CH—CH—CH— and form an aromatic group;

any bond having dotted line (------) represents independently from each other either a carbon-carbon single bond or a carbon-carbon double bond; and any wavy line represents independently from each other a carbon-carbon bond and which when linked to the carbon-carbon double bond is either in the Z- or in the E-configuration.

The compound of the formula (II), the base catalyst and ring closure step as well their preferred embodiments have been already discussed above in great detail for the process.

It has been further found that the compound of the formula (I-A) or (I-C) or (III-A) or (III-C) or (IV-A) or (IV-C) has antioxidative properties.

Hence, in a further aspect, the invention relates to the use of the compound of the formula (I-A) or (I-C) or (III-A) or (III-C) or (IV-A) or (IV-C) as an antioxidant.

(I-A)

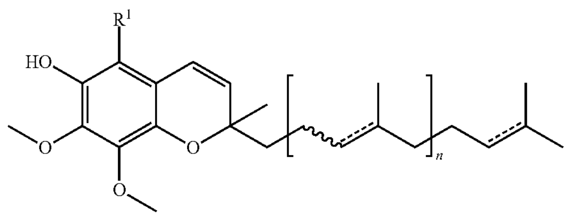

n = 0-9, particularly n = 8

(I-C)

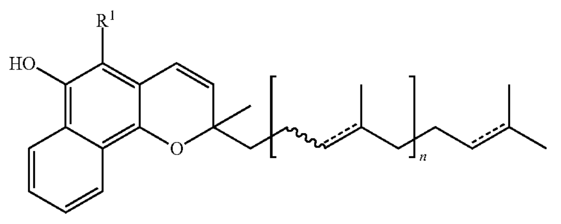

n = 0-12

(III-A)

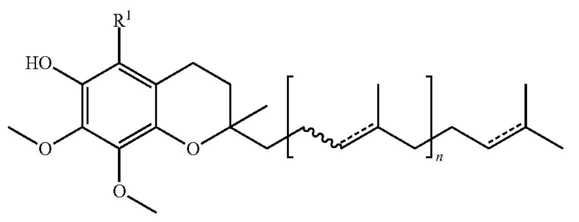

n = 0-9, particularly n = 8

(III-C)

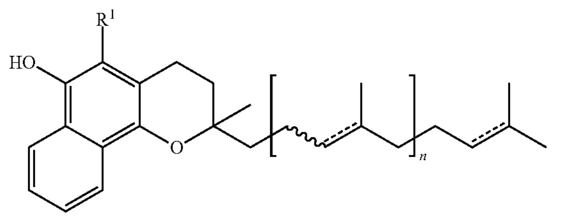

n = 0-12

(IV-A)

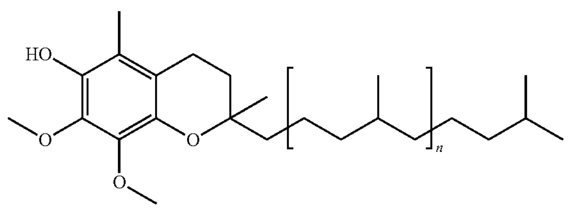

n = 0-9, particularly n = 8

-continued (IV-C)

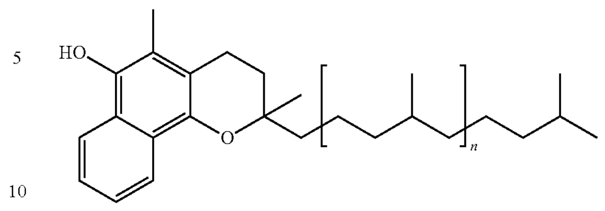

n = 0-12 wherein $R^1$ represents hydrogen or a methyl group.

The compounds of the formula (I-A) or (I-C) or (III-A) or (III-C) or (IV-A) or (IV-C) as well their preferred embodiments have been already discussed above in great detail for the process.

Several compounds disclosed in this document are new. Due to their suitability for the disclosed processes and uses said compound are not only new but also inventive.

Hence, in a further aspect, the invention relates particularly to the compounds of the formula (I-As) or (I-Cis) or (III-Cis) or (IV-Cs)

(I-As)

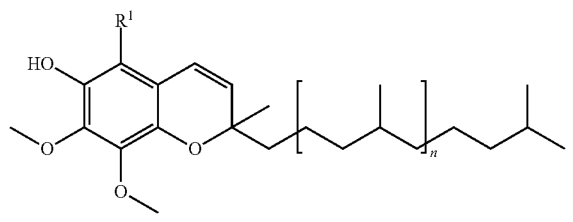

wherein n = 3-9, particularly n = 8

(I-Cis)

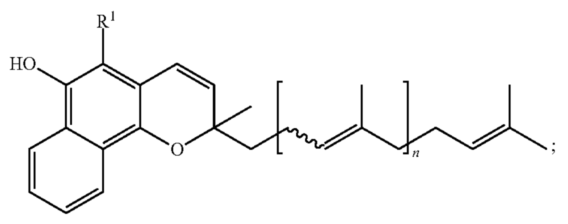

wherein n = 1-12, particularly n = 2-5

(III-Cis)

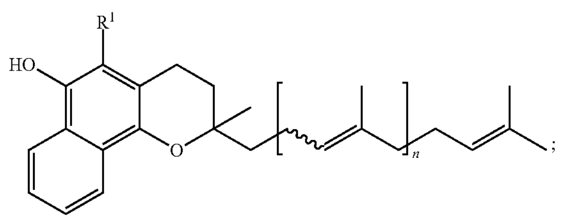

wherein n = 3-6, particularly n = 5

-continued (IV-Cs)

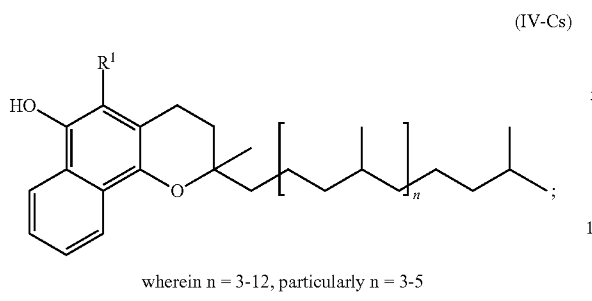

wherein n = 3-12, particularly n = 3-5 and wherein $R^1$ represents hydrogen or a methyl group;

any bond having dotted line ( ------ ) represents independently from each other either a carbon-carbon single bond or a carbon-carbon double bond; and any wavy line represents independently from each other a carbon-carbon bond and which when linked to the carbon-carbon double bond is either in the Z- or in the E-configuration.

Examples

The present invention is further illustrated by the following experiments.

Formation of (E)-2-(4,8-dimethylnona-3,7-dien-1-yl)-2,5,7,8-tetramethyl-2H-chromen-6-ol 4-hydroxy-2,3,6-trimethyl-5-((6E)-3,7,11-trimethyldodeca-2,6,10-trien-1-yl)phenyl acetate (2.0 g, 4.74 mmol) was mixed with 50 mL diethyl ether and cooled to 5° C. Then lithium aluminium hydride (2 M in THF) (2.96 ml, 5.92 mmol) was added, after 3.5 h at 0-24° C. the reaction was stopped by adding 40 mL 4 N HCl. The organic phase has been washed once with 40 mL brine and 0.2 g sodium dithionite, and dried over $MgSO_4$. After filtration and evaporation, 2,3,5-trimethyl-6-((6E)-3,7,11-trimethyldodeca-2,6,10-trien-1-yl)benzene-1,4-diol was isolated in a yield of 85%.

The 2,3,5-trimethyl-6-((6E)-3,7,11-trimethyldodeca-2,6,10-trien-1-yl)benzene-1,4-diol was dissolved in diethyl ether (7.5 mL) and 1.5 equivalent silver oxide and 46 μL of acetic acid were added and the mixture was stirred at room temperature for 2 hours. After filtration and purification by chromatography (neutral silica) 2,3,5-trimethyl-6-((6E)-3,7,11-trimethyldodeca-2,6,10-trien-1-yl)cyclohexa-2,5-diene-1,4-dione has been isolated in a yield of 88%.

2,3,5-trimethyl-6-((6E)-3,7,11-trimethyldodeca-2,6,10-trien-1-yl)cyclohexa-2,5-diene-1,4-dione (1.27 g (3.29 mmol)) and 18 ml toluene and 0.15 ml (0.988 mmol) 1,8-diazabicyclo[5.4.0]undec-7-ene (=DBU) were added and stirred under reflux (110° C.) for 20 hours to form (E)-2-(4,8-dimethylnona-3,7-dien-1-yl)-2,5,7,8-tetramethyl-2H-chromen-6-ol in 86.5% yield.

Experimental Series 1

Geranylgeranyl trimethyl benzoquinone (purity 97%) (0.5 g (1.183 mmol)) and 6 ml toluene and the respective amount of the basic catalyst as given in table 1 were added and stirred under reflux (110° C.) for the reaction time given in table 1 to yield the 2,5,7,8-tetramethyl-2-(4,8,12-trimethyltrideca-3,7,11-trien-1-yl)-2H-chromen-6-ol (3,4-dehydro-α-tocotrienol) in conversion and yield as indicated in table 1.

TABLE 1

Different basic catalysts

| Example | Basic catalyst[1] | $pk_a$ | Base/quinone [mol/mol] | Reaction Time [h] | Conversion [%] | Yield [%] |
|---|---|---|---|---|---|---|
| 1 | DMAP | 9.2[2], 9.7[3] | 1/10 | 48 | 98 | 93 |
| 2 | DBU | 12[2], 13.28[3] | 1/10 | 2 | >99 | 99 |
| 3 | DBU | 12[2], 13.28[3] | 1/100 | 6 | >99 | 99 |
| 4 | DBU | 12[2], 13.28[3] | 1/200 | 24 | >99 | 100 |
| 5 | quinuclidine | 11[2], 10.95[3] | 1/100 | 6 | >99 | 95 |
| 6 | sparteine | 9.45[2] | 1/10 | 6 | 98 | 97 |
| 7 | morpholine | 8.36[2], 8.49[3] | 1/10 | 48 | 39 | 39 |
| 8 | TEA | 7.76[3] | 1/10 | 20 | 7 | 4 |
| 9 | pyridine | 5.23[2], 5.23[3] | 1/10 | 20 | <1 | n.a.[4] |

[1]DMAP = 4-(dimethylamino)pyridine; DBU = 1,8-diazabicyclo[5.4.0]-undec-7-ene; TEA = Triethanolamine
[2]H. Ripin; D. A. Evans (2002). "$pK_a$'s of Nitrogen Acids" organicchemistrydata.org/hansreich/resources/pka/pka_data/evans_pKa_table.pdf
[3]www.aatbio.com/data-sets/pka-and-pkb-reference-table
[4]n.a. = not applicable The results of table 1 show that all bases used in catalytical amounts show formation of the desired product, i.e. 3,4-dehydro-α-tocotrienol. The majority of examples show that a very high conversion and yields of more than 94% can be obtained. Furthermore, examples 7 and 8 and 9 of table 1 show that particularly basic catalysts the conjugated acid of which has a $pK_a$ of lower than 8.6 lead to lower conversion and yield. The experiments also reveal that pyridine shows particularly low conversion at catalytic concentrations. The comparison of example 2 and 3 shows that, despite of a tenfold lower concentration, still an extraordinary high conversion and yield can be obtained.

Partial Hydroqenation 3,4-Dehydro-α-tocotrienol (=2,5,7,8-tetramethyl-2-(4,8,12-trimethyltrideca-3,7,11-trien-1-yl)-2H-chromen-6-ol) as prepared above has been quantitatively hydrogenated to α-tocotrienol (=2,5,7,8-tetramethyl-2-(4,8,12-trimethyltrideca-3,7,11-trien-1-yl)chroman-6-ol according the procedure disclosed in the last paragraph on page 2524 of Schudel, Mayer, Isler, Helv. *Chim. Acta* 46, 2517-2526 (1963), the identity of which could be verified by NMR.

Complete Hydroqenation 3,4-Dehydro-α-tocotrienol (=2,5,7,8-tetramethyl-2-(4,8,12-trimethyltrideca-3,7,11-trien-1-yl)-2H-chromen-6-ol) as prepared above has been quantitatively hydrogenated to α-tocophenol (=2,5,7,8-tetramethyl-2-(4,8,12-trimethyltridecyl)-chroman-6-ol) by hydrogen on Pd/C according to the last paragraph on page 888 of Kabbe and Heitzer, *Synthesis* 1978; 12, 888-889, the identity of which could be verified by NMR.

Experimental Series 2 In a further series, 0.46 g (1.098 mmol) geranylgeranyl trimethyl benzoquinone (purity 97%) and amounts of toluene as given in table 2 and 5.49 μmol DBU (1/200) were added and stirred under reflux (110° C.) for 24 hours to yield the 2,5,7,8-tetramethyl-2-(4,8,12-trimethyltrideca-3,7,11-trien-1-yl)-2H-chromen-6-ol (3,4-dehydro-α-tocotrienol) in conversion and yield as indicated in table 2.

TABLE 2

Different concentrations of the quinone (geranylgeranyl trimethyl benzo-quinone) in toluene for the ring closure reaction using DBU as base.

| Example | Base/ quinone [mol/mol] | Amount of toluene [ml] | Concentration quinone [M] | Conversion [%] | Yield [%] |
|---|---|---|---|---|---|
| 4 | 1/200 | 6 | 0.18 | 99.2 | 100 |
| 10 | 1/200 | 3 | 0.37 | 98.9 | 98.4 |
| 11 | 1/200 | 1.5 | 0.73 | 98.6 | 98.6 |

Experimental Series 3

In a further series, 0.46 g (1.098 mmol) geranylgeranyl trimethyl benzoquinone (purity 97%) and 6 ml toluene and 4.7 mg ground solid NaOH (0.1098 mmol, 10 mol % (relative to geranylgeranyl trimethyl benzoquinone)) in the presence of 3.5 mg of tetrabutylammonium bromide (1 mol % (relative to geranylgeranyl trimethyl benzoquinone)) were added and stirred under reflux (110° C.) for the reaction time given in table 2 to yield the 2,5,7,8-tetramethyl-2-(4,8,12-tri-methyltrideca-3,7,11-trien-1-yl)-2H-chromen-6-ol (3,4-dehydro-α-tocotrienol) in conversion and yield as indicated in table 3.

TABLE 3

Solid NaOH as basic catalyst.

| Example | Base/quinone [mol/mol] | Reaction Time [h] | Conversion [%] | Yield [%] |
|---|---|---|---|---|
| 12 | 1/10 | 1 | 86 | 82.4 |
| 13 | 1/10 | 16 | 95 | 92.6 |
| 14 | 1/10 | 36 | 96 | 93.3 |

The invention claimed is:

1. A process of manufacturing the compound of formula (I):

(I)

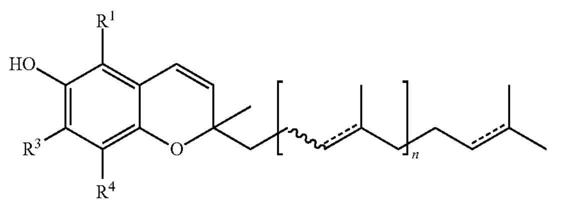

wherein the process comprises a ring closing step of the compound of formula (II):

(II)

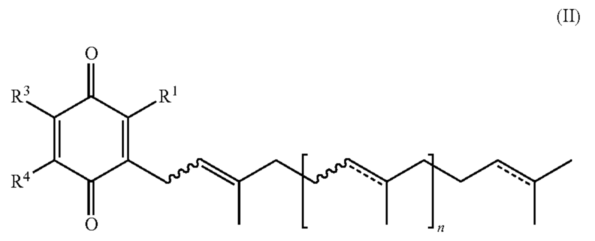

in the presence of a basic catalyst to yield the compound of formula (I), wherein n=0 or 1 or 2 or 3 or 4 or 5 or 6 or 7 or 8 or 9 or 10 or 11 or 12;

$R^1$ represents hydrogen or a methyl group;

$R^3$ and $R^4$ either represent independently from each other hydrogen or methyl group or methoxy group or represent together a —CH—CH—CH— and form an aromatic group;

any bond having dotted line (------) represents independently from each other either a carbon-carbon single bond or a carbon-carbon double bond; and any wavy line represents independently from each other a carbon-carbon bond and which when linked to the carbon-carbon double bond is either in the Z- or in the E-configuration; and wherein a molar ratio of the basic catalyst to the compound of formula (II) is 1:1,000 to 1:5.

2. The process according to claim 1, wherein $R^1$=$R^3$=$R^4$=$CH_3$.

3. The process according to claim 1, wherein the basic catalyst is either an organic amine or a metal hydroxide or carbonate.

4. The process according to claim 1, wherein a conjugated acid of the basic catalyst has a pKa of between 8.6 and 15.7 measured in water.

5. The process according to claim 1, wherein the basic catalyst is selected from the group consisting of 4-dimethylaminopyridine (=DMAP), 1,8-diazabicyclo[5.4.0]undec-7-ene (=DBU), 1,5-diazabicyclo[4.3.0]non-5-ene (=DBN), 1,4-diazabicyclo[2.2.2]octane (=DABCO), 1-azabicyclo[2.2.2]octane (=quinuclidine) and sparteine.

6. The process according to claim 1, wherein the compound of formula (I) is a compound of formula (I-BB) and the compound of formula (II) is a compound of formula (II-BB):

(I-BB)

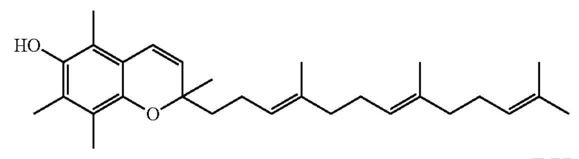

(II-BB)

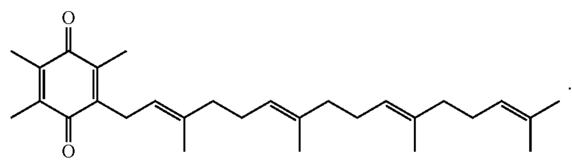

7. The process according to claim 1, wherein the ring closing step is performed in a hydrocarbon solvent.

8. The process according to claim 7, wherein the hydrocarbon solvent is toluene.

9. The process according to claim 1, wherein the molar ratio of the basic catalyst to the compound of formula (II) is 1:100 to 1:10.

10. The process according to claim 1, wherein the basic catalyst is an organic tertiary amine or an alkali metal hydroxide.

11. The process according to claim 1, wherein the basic catalyst has a $pK_a$ of between 9 and 15.7 measured in water.

12. A process of manufacturing a compound of formula (III):

(III)

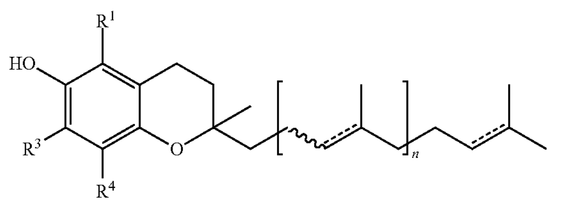

wherein the process comprises:

a) manufacturing the compound of formula (I) by the process according to claim 1; and thereafter b) partially hydrogenating the compound of formula (I) by contacting the compound of formula (I) with a hydrogenating agent suitable for partial hydrogenation to yield the compound of formula (III), wherein n, $R^1$, $R^3$, $R^4$, any bond having a dotted line ( ------ ) and any wavy line are as stated previously.

13. A process of manufacturing a compound of formula (IV):

(I)

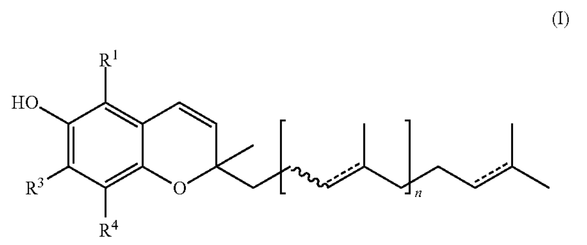

comprising the steps a) manufacturing the compound of formula (I) by the process according to claim 1; and thereafter b) hydrogenating the compound of the formula (I) by contacting the compound of formula (I) with a hydrogenating agent to yield the compound of the formula (IV), wherein n, $R^1$, $R^3$ and $R^4$ are as stated previously.

* * * * *